(12) United States Patent
Saar et al.

(10) Patent No.: US 6,747,060 B2
(45) Date of Patent: Jun. 8, 2004

(54) NON-NATURAL GALANIN RECEPTOR LIGANDS

(75) Inventors: Kulliki Saar, Stockholm (SE); Tamas Bartfai, La Jolla, CA (US); Ulo Langel, Stockholm (SE); Gerd Hallnemo, S˝dertalje (SE); Sven Hellberg, S˝dertalje (SE)

(73) Assignee: Kemia, Inc., San Diego, CA (US)

( * ) Notice: Subject to any disclaimer, the term of this patent is extended or adjusted under 35 U.S.C. 154(b) by 0 days.

(21) Appl. No.: 10/155,376

(22) Filed: May 24, 2002

(65) Prior Publication Data

US 2003/0055000 A1 Mar. 20, 2003

Related U.S. Application Data

(60) Provisional application No. 60/372,237, filed on Apr. 12, 2002.

(51) Int. Cl.[7] .............................................. A61K 31/35
(52) U.S. Cl. ...................................... 514/457; 549/288
(58) Field of Search ........................... 549/288; 514/457

(56) References Cited

PUBLICATIONS

Saar, K et al, 'Anticonvulsant activity of a nonpeptide galanin receptor agonist' Proceedings of the National Academy of Sciences of the United States of America (2002), 99(10), 7136–7141.*
Salvati, Luca et al, 'Modulation of the catalytic activity of cruzipain, the major cysteineproteinase from *Trypanosoma cruzi*, by temperature and pH' European Journal of Biochemistry (2001), 268(11), 3253–3258.*
McKie, J. H., 'Specific peptide inhibitors of trypanothione reductase with backbonestructures unrelated to that of substrate: potential rational drug design lead frameworks' Amino Acids (2001), 20(2), 145–153, CA 135:204909.*
Bartfai and Langel, "Galanin receptor ligands as potential therapeutic agents in depression and neurodegeneration." Eur. J. Med. Chem., 30: S163–S174, 1995.
Bartfai, T., "Galanin: A neuropeptide with important central nervous system actions" in Psychopharmacology: The Fourth Generation of Progress, edited by Bloom and Kupfer, New York: Raven Press, 1995, p. 563–571.
Chu, et al., "A new fungal metabolite, Sch 202596, with inhibitory activity in the galanin receptor GALR1 assay." Tetrahedron Letter, 38: 6111–6114, 1997.
Land et al., "Linear and cyclic N–terminal galanin fragments and analogs as ligands at the hypothalamic galanic receptor." Int. J. Peptide Protein Res., 38: 267–272, 1991.
Land et al., "Assay for galanin receptor." In Methods in Neurosciences, edited by P.Michael Conn, San Diego: Academic Press, vol. 5: 225–234, 1991.
Langel and Bartfai, "Chemistry and molecular biology of galanin receptor ligands." Ann. NY Acad. Sci., 863: 86–93, 1998.

Mazarati et al., "Anticonvulsant activity of the first systemically active galanin receptor agonist." Abstracts Scoiety for Neuroscience, 31st annual meeting, San Diego, CA., Nov. 10–15, 2001, 27: 2005.
Mazarati et al., "Anticonvulsive effects of galanin administered into the central newvous system upon the picrotoxin–kindled seizure syndrome in rats." Brain Research, 589:164–166, 1992.
Mazarati et al., "Galatin modulation of seizures and seizure modulation of hippocampal galanin in an animal model of status epilepticus." J.Neuroscience, 18:10070–10077, 1998.
Mazarati et al., "Modulation of hippocampal excitability and seizures by galanin." J. Neuroscience, 20: 6276–6281, 2000.
Pooga et al., "Cell penetrating PNA constructs regulate galanin receptor levels and modify pain transmission in vivo." Nature Biotechnology, 16: 857–861, 1998.
Scott et al., "2,3–Dihydro–dithiin and –dithiepine–1,1,4,4–tetroxides: small molecule non–peptide antagonists of the human galanin hGAL–1 receptor." Bioorg. Med. Chem., 8: 1383–1391, 2000.
Tatemoto et al., "Galanin–a novel biologically active peptide from porcine intestine." FEBS Letters, 164: 124–128, 1983.
Valkna, et al., "Effects of chimeric galanin receptor ligands on basal adenylate cyclase activity in rat ventral hippocampal membranes." Protein Peptide Letters, 2: 267–274, 1995.
Valkna et al., "Differential regulation of adenylate cyclase activity in rat ventral and dorsal hippocampus by rat galanin." Neuroscience Letters, 187: 75–78, 1995.
Xu et al., "Electrophysiological evidence for a hyperpolarizing galanin (1–15)– selective receptor on hippocampal CA3 pyramidal neurons." Proc. Nat. Acad. Sci. USA, 96: 14583–7, 1999.
Young and Kuhar, "A new method for receptor autoradiography: [3H]opioid receptors in rat brain." Brian Research, 179: 255–270, 1979.

(List continued on next page.)

*Primary Examiner*—Amelia Owens
(74) *Attorney, Agent, or Firm*—Foley & Lardner; Richard J. Warburg

(57) ABSTRACT

Compounds which are non-natural galanin receptor ligands are disclosed. The ligands are of small size, have agonist or antagonist galanin activity and may cross the blood-brain barrier to displace galanin from galanin receptors. The ligands are useful as medicaments for treatment of convulsions (e.g. in epilepsy), diseases and disorders related to endocrinology (e.g., growth hormone, insulin or prolactin release), tumors expressing galanin receptors, feeding disorders pain, allodynia, psychiatric disorders such as depression (involving e.g., noradrenaline or serotonin), cognitive disorders (e.g. Alzeimer's disease), and the like.

59 Claims, 5 Drawing Sheets

OTHER PUBLICATIONS

Zini et al., "Galanin reduces release of endogenous excitatory amino acids in the rat hippocampus." Eur. J. Pharmacol. Molec. Pharm., 245: 1–7, 1993.

Cain et al., "Production, Purification, and Characterization of Recombinant Prohormone Convertase 5 from Baculovirus–Infected Insect Cells." Protein Expression and Purification, 24: 227–233, 2002.

Floren et al., "Galanin receptor subtypes and ligand binding." Neuropeptides, 34(6): 331–337, 2000.

STN International, file ZCAPLUS, ZCAPLUS accession No. 2001:9514, Document No. 134:189890. Abe et al., "Design and synthesis of sensitive fluorogenic substrates specific for Lys–gingipain." Journal of Biochemistry (Tokyo) 128(5): 877–881, 2000. Abstract.

STN International, file ZCAPLUS, ZCAPLUS accession No. 1980:193362, Document No. 92:193362. Iwanaga et al., "Fluorogenic peptide substrates for proteases in blood coagulation, kallikrein–kinin and fibrinolysis systems." Adv. Exp. Med. Biol. (1979), Volume Date 1978, 120A(Kinins 2: Biochem., Pathophysiol., Clin. Aspects) 147–163. Abstract.

International Search Report for PCT Application No. PCT/SE02/01002.

* cited by examiner

P<0.05: 1 *vs.* Control, 2 *vs.* equimolar amount of Galanin

NON-NATURAL GALANIN RECEPTOR LIGANDS

The present invention relates to non-natural galanin receptor ligands which can function as agonists and antagonists of galanin and can be used to treat diseases or conditions in which galanin plays a role.

BACKGROUND OF THE INVENTION

Galanin[1] is a 29/30 amino acid long neuroendocrine peptide that potently affects seizure activity, cognition, mood, feeding, and pain threshold[2-6]. Galanin-overexpressing mice have increased resistance to status epilepticus, while galanin knockout mice have lowered seizure threshold[6]. These results indicate that endogenous galanin is an important determinant of hippocampal excitability and of seizure threshold. The importance of galanin agonists for seizure control may arise from their ability to act at both pre- and postsynaptic sites to reduce excitability, to inhibit glutamate but not GABA release[7], and to hyperpolarize both dentate granule cells and CA1–CA3 pyramidal cells by opening K+-channels[8], dampening seizure activity. Although intracerebroventricularly injected galanin blocks seizures[5] in mice, this large peptide is unable to cross the blood-brain barrier and is rapidly degraded.

To date, there are only two reports on non-peptide ligands for galanin receptors, which behave as antagonists: spirocoumaranon[9] (Sch 202596; IC50 of 1.4 $\mu$M at human GalR1) and dithiipin-1,1,4,4-tetroxide[10] (IC50 of 0.17 $\mu$M at human GalR1), despite extensive random screening efforts at six large pharmaceutical companies.

SUMMARY OF THE INVENTION

In accordance with the present invention, there are provided low molecular weight ligands for galanin receptor(s) having the formula:

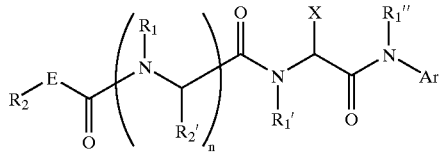

wherein:

$R_1$, $R_1'$, and $R_1''$ are each independently hydrogen or lower alkyl, $R_2$ and $R_2'$ are each independently an optionally substituted hydrocarbyl moiety containing at least about four carbon atoms, E is optional, and, if present, is O, N or S, X is a hydrocarbyl moiety bearing at least one substituent, wherein at least one of said substituents bears a positive charge, Ar is an optionally substituted aromatic or heteroaromatic moiety having at least about three carbon atoms, and n is 1, 2 or 3.

A preferred embodiment of the above compounds has been given the name "galnon": Fmoc-Cha-Lys-amidomethyl coumarin (according to IUPAC systematic nomenclature: 1-[5-amino-1-(4-methyl-2-oxo-2H-chromen-7-ylcarbamoyl)-pentylcarbamoyl]-2-cyclohexyl-ethyl-carbamic acid 9H-fluoren-9-ylmethyl ester).

The galanin receptor ligands of the invention are characterized in having galanin agonist or antagonist activity, are generally 700 daltons or less in molecular weight, and have the ability to cross the blood-brain barrier.

Also provided herein are various uses for the invention ligands, including in vitro and in vivo analysis of galanin receptor structure and function, and use in treating a variety of diseases and conditions in which galanin plays a role. Such diseases or conditions include convulsions such as in epilepsy, growth, diabetes, pain, allodynia psychiatric states, cognition, and feeding. For such uses, the invention compounds can be formulated with an appropriate excipient(s) for pharmaceutical administration to a mammalian patient.

These and other aspects of the invention will be addressed in greater detail below.

Figure 1:
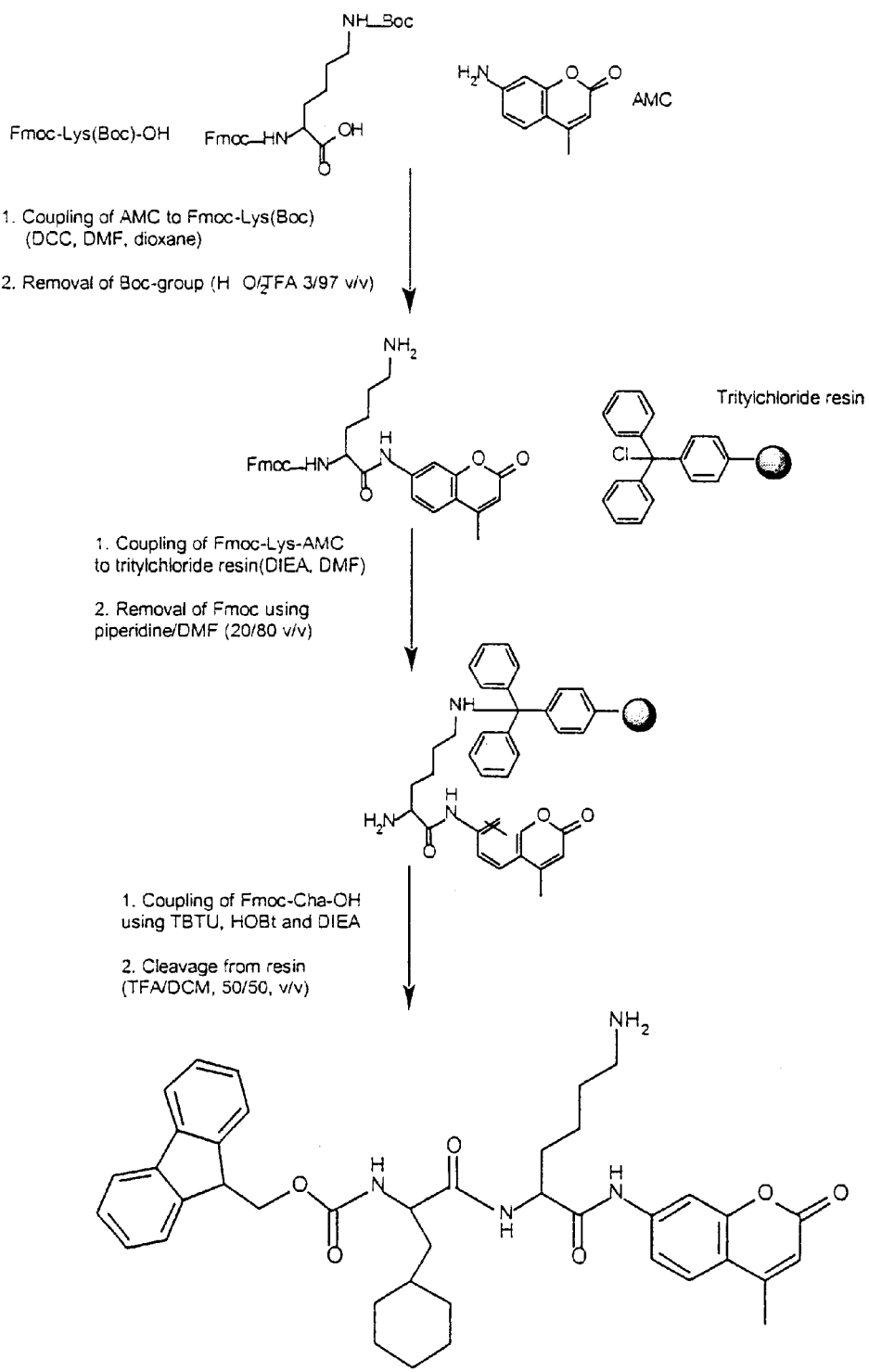
FIG. 1 depicts a scheme for synthesis of galnon.

a: Effect of galnon on PTZ-induced seizures. Galanin (O), galnon ( ) treated animals, and controls (♦). Asterisks indicate p<0.01 versus control.

b: Effects of co-administration of M35 and galnon on PTZ-induced seizures. Animals treated with M35 (■), with M35 and galnon (□); controls (♦). Asterisks indicate p<0.05 versus control.

FIG. 3. Effects of galnon on self sustaining status epilepticus ("SSSE") induced by 30 min. of PPS. Data are presented as mean±SEM. Inserts show maximal seizure scores (mean±SEM).

a: Intrahippocampal injection of galnon 10 min. after the end of PPS attenuated SSSE in a dose dependent manner.

b. In a model of SSSE in rats, anticonvulsant effects of both galanin and galnon were attenuated by GalR antagonist M35.

c. Injection of M35 (5 nM) into the hippocampus facilitated the development of SSSE. This effect was attenuated by co-administration with galnon.

DESCRIPTION OF THE INVENTION

In accordance with the present invention, there are provided low molecular weight ligands for galanin receptor(s) having the formula:

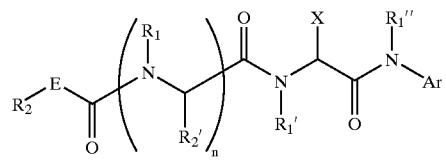

wherein:

$R_1$, $R_1'$, and $R_1''$ are each independently hydrogen or lower alkyl, $R_2$ and $R_2'$ are each independently an optionally substituted hydrocarbyl moiety containing at least about four carbon atoms, E is optional, and, if present, is O, N or S, X is a hydrocarbyl moiety bearing at least one substituent, wherein at least one of said substituents bears a positive charge, Ar is an optionally substituted aromatic or heteroaromatic moiety having at least about three carbon atoms, and n is 1, 2 or 3.

It is understood that all stereoisomers of the above-identified structure are contemplated for use in the practice of the present invention.

As employed herein, "hydrocarbyl" refers to alkyl, substituted alkyl, cycloalkyl, substituted cycloalkyl, alkenyl, substituted alkenyl, alkynyl, substituted alkynyl, aryl, or substituted aryl.

As employed herein, "alkyl" refers to hydrocarbyl radicals having 1 up to about 20 carbon atoms, preferably 2–10 carbon atoms; and "substituted alkyl" comprises alkyl groups further bearing one or more substituents in place of a hydrogen atom selected from hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, oxo, cyano, nitro, amino, amido, C(O)H, acyl, oxyacyl, carboxyl, carbamate, sulfonyl, sulfonamide, or sulfuryl.

As employed herein, "lower alkyl" refers to hydrocarbyl radicals having 1 up to 6 carbon atoms.

As employed herein, "cycloalkyl" refers to cyclic ring-containing groups containing in the range of 3 up to about 10 carbon atoms, and "substituted cycloalkyl" refers to cycloalkyl groups further bearing one or more substituents as set forth above. Cycloalkyl groups as defined herein also refer to bicyclo- or tricycloalkyl groups, such as, for example, 2.2.1.-bicycloheptane, or adamantane.

As employed herein, "alkenyl" refers to straight or branched chain hydrocarbyl groups having at least one carbon-carbon double bond, and having in the range of 2 up to about 12 carbon atoms, and "substituted alkenyl" refers to alkenyl groups further bearing one or more substituents as set forth above.

As employed herein, "cycloalkenyl" refers to cyclic ring-containing groups containing in the range of 3 up to about 10 carbon atoms, wherein the cyclic ring-containing group contains at least one carbon-carbon double bond. "Substituted cycloalkenyl" refers to cycloalkenyl groups further bearing one or more substituents as set forth above.

As employed herein, "alkynyl" refers to straight or branched chain hydrocarbyl groups having at least one carbon-carbon triple bond, and having in the range of 2 up to about 12 carbon atoms, and "substituted alkynyl" refers to alkynyl groups further bearing one or more substituents as set forth above.

As employed herein, "aromatic" is a cyclic organic molecule which contains $4n+2\pi$ electrons where $n=1,2,3$ etc. Aromatic molecules are typically stable and are depicted as a planar ring of atoms with resonance structures that consist of alternating double and single bonds, e.g. benzene.

As employed herein, "heteroaromatic" refers to aromatic groups containing one or more heteroatoms (e.g., N, O, S,) as part of the ring structure, and having in the range of 3 up to 10 carbon atoms, optionally bearing one or more substituents as set forth above.

As employed herein, "heterocyclic" refers to cyclic (i.e., ring-containing) groups containing one or more heteroatoms (e.g., N, O, S) as part of the ring structure, and having in the range of 3 up to 10 carbon atoms and "substituted heterocyclic" refers to heterocyclic groups further bearing one or more substituents as set forth above.

It should be understood from the above that a substituted alkyl, substituted cycloalkyl, substituted alkenyl, substituted alkynyl, or substituted aryl radicals may comprise as the substituent, cycloalkyl, alkenyl, alkynyl or, alternatively, substituted cycloalkyl, substituted alkenyl, substituted alkynyl, or substituted aryl. Thus, a substituted form of hydrocarbyl moiety may have, as the substituent, another substituted form of hydrocarbyl, and so forth. In general, if a substituted form of hycrocarbyl is present, such hydrocarbyl is preferably not further substituted or if substituted, the substituent comprises only a limited number of substituted hydrocarbyl moieties, preferably 1, 2, 3, 4 or 5 such substitutions.

In one aspect of the invention, $R_2$ is a hydrophobic hydrocarbyl moiety which imparts steric bulk and/or hydrophobicity to the ligand. The hydrophobic hydrocarbyl moiety may be cyclic comprising one or more rings (e.g., mono, di, tri cyclic). Such cyclic hydrocarbyl moiety may be further substituted as described above (e.g., alkyl, alkenyl, or alkynyl moiety). In some cases, the further substituent (e.g., a methylene group) may be a link between the ring of $R_2$ and E. The cyclic hydrocarbyl moiety may be cycloalkyl, heterocyclic, aromatic, or heteroaromatic with mixtures of ring types possible when two more rings are involved. The hydrophobic hydrocarbyl moiety also may be a branched hydrocarbon. As employed herein, a branched hydrocarbon has at least one hydrocarbon branch point, which is a carbon atom attached to at least three carbon atoms. A tertiary butyl group is an example of branched chain hydrocarbyl moiety. The carbon atoms after the branch points also can be branched. $R_2$ also may be a combination of cyclic hydrocarbon and branched hydrocarbon. In a preferred embodiment, $R_2$ comprises fluorenyl, adamantyl, or phenyl. Most preferably $R_2$ comprises fluorenyl.

In another aspect of the invention, $R_2'$ is a hydrophobic hydrocarbyl moiety which may or may not impart steric bulk to the ligand. In order to impart a degree of hydrophobicity to the ligand, $R_2'$ typically contains at least about six carbon atoms. In one embodiment, $R_2'$ is an optionally substituted straight or branched chain hydrocarbyl moiety. In an alternative embodiment, $R_2'$ is an optionally substituted cyclic moiety, such as, for example, cycloalkyl, heterocyclic (e.g., pyridone), aromatic, or heteroaromatic. If a cyclic moiety is involved, it is preferably a single ring, however, $R_2'$ may comprise multiple rings such as cycloalkyl, heterocyclic, aromatic, or heteroaromatic or combinations thereof. Such cyclic hydrocarbyl moiety may further comprise an alkyl, alkenyl, or alkynyl moiety. In some cases, the further substituent (e.g., a methylene group) may link the ring of $R_2'$ to the compound backbone. Preferably, $R_2'$ comprises cyclohexylmethyl or benzyl. In addition, those skilled in the art will recognize that $R_2'$ may be incorporated into invention compounds as a side chain of a hydrophobic amino acid, such as, e.g., tyrosine, typtophan or dihydroxyphenyl phenylalanine. The side chain may be in the D or L configuration.

In a further aspect of the invention, X is a straight or branched chain alkyl, containing at least one substituent bearing a positive charge. Those skilled in the art recognize that there are a variety of well-known substituents with the ability to bear, under appropriate conditions (e.g., low pH) a positive charge, such as, for example, hydroxy groups, amines, or thiols which when positively charged are referred to as hydronium, ammonium and sulfonium, respectively. In addition, those skilled in the art recognize that X may be incorporated into invention compounds as a side chain of an amino acid, such as, e.g., lysine, arginine, histidine, asparagine, or glutamine. In a most preferred embodiment, the side chain is from lysine. The side chain may be in the D or L configuration.

In yet another aspect of the invention, Ar is an optionally substituted aromatic or heteroaromatic moiety having at least about three carbon atoms. In one embodiment, Ar comprises an optionally substituted aromatic, such as, for example, phenyl or naphthyl. In an alternative embodiment, Ar comprises an optionally substituted heteroaromatic. Preferably, the heteroaromatic comprises chromenyl, furyl, thiophenyl, oxadiazolyl, benzoxazyl, benzofuryl, benzodioxolyl, imidazolyl, benzimidazolyl, pyrrolyl, thienyl, thiazolyl, oxazolyl, isoxazolyl, triazolyl, benzotriazolyl, indolyl, pyrimidinyl, pyrazolyl, quinolinyl, isoquinolinyl, quinazolinyl, or pyridyl. Most preferably, Ar comprises chromenyl.

A particular compound suitable for use in the practice of the present invention has been given the name "galnon": Fmoc-Cha-Lys-amidomethyl coumarin (according to ITU-PAC systematic nomenclature: 1-[5-amino-1-(4-methyl-2-oxo-2H-chromen-7-ylcarbamoyl)-pentylcarbamoyl]-2-cyclohexyl-ethyl-carbamic acid 9H-fluoren-9-ylmethyl ester). This agonist of the invention inhibits adenylate cyclase activity in vitro, and attenuates pentylenetetrazole-induced seizures in vivo when administered systemically. These findings introduce and support the efficacy of a new class of antiepileptic agents, which are effective in inhibiting a variety of seizure types. This particular galanin receptor agonist has the structure:

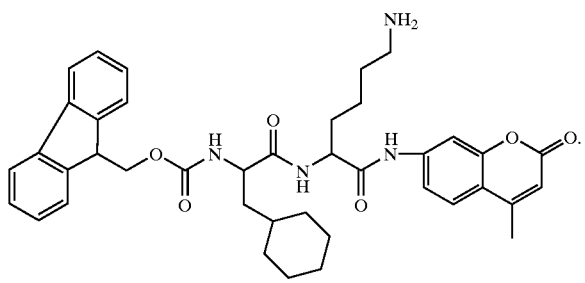

The above compound from left to right is composed of a bulky hydrophobic group (i.e., the Fmoc group) coupled to a hydrophobic amino acid residue, which is coupled to an amino acid residue with a protonated side-chain, which is finally coupled to an aromatic amine. In addition, this compound has the ability to cross the blood-brain barrier and to displace galanin from galanin receptors.

In an alternative embodiment, the bulky hydrophobic group is derived from fluorenylcarboxylic acid, as depicted in the exemplary structure shown below:

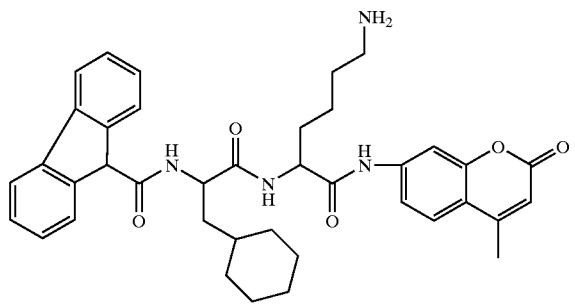

In embodiment of the invention a galanin receptor ligand L-138 has the formula:

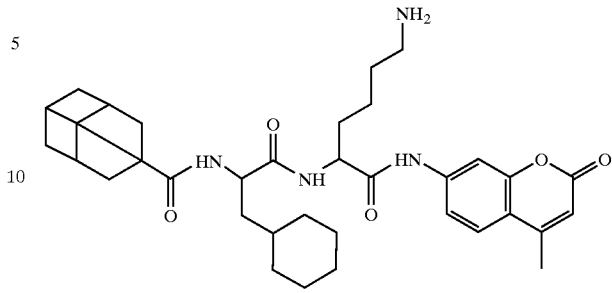

In another embodiment of the invention a galanin receptor ligand L-131 has the formula:

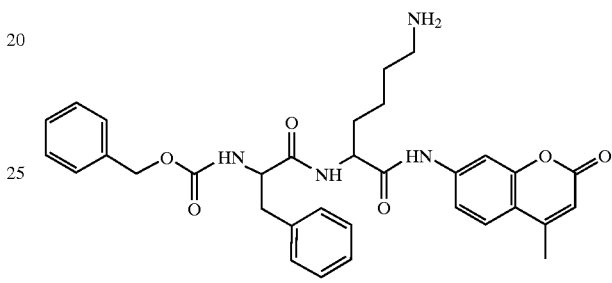

It should be understood that the cyclohexylalanine group of the compound L138 and galnon, the phenylalanine group of compound L131, and the lysine group of compounds L131, L138 and galnon maybe in D-, L- or DL- form.

Galanin receptor ligands of the invention non-natural compounds that have the ability to displace galanin from its receptor. A "receptor ligand" as used herein with respect to galanin is a non-natural compound generally small in size, having a molecular weight of 10,000 daltons (Da) or less, preferably 1,000 Da or less and more preferably 700 Da or less. Galanin receptor ligands bind to the galanin receptor and displace natural galanin, exhibiting an affinity for the receptor in the micromolar range or lower (e.g. nanomolar).

Galanin receptor ligands of the invention have agonist or antagonist activity. As employed herein, a galanin receptor ligand has agonist activity with respect to the galanin receptor if it activates the galanin receptor in a manner that is similar to that achieved with native galanin. A galanin receptor ligand with antagonist activity blocks or inhibits activation of the galanin receptor by native galanin. The galanin receptor ligands including galnon, L131 and L138 are galanin agonists.

Galanin receptor ligands of the invention preferably have the property of being able to cross the blood brain barrier. As employed herein, the blood brain barrier refers to the endothelial cell lining of blood vessels located in the central nervous system. Galanin receptor ligands can cross the blood brain barrier following administration into blood by virtue of their small size (generally about 700 Da or less) and hydrophobic character. Alternatively, the invention compounds may cross the blood brain barrier by coupling them to a peptide naturally transfers by receptor-mediated peptide transport (e.g. insulin).

Galanin receptor ligands of the invention have utility for dissecting the mechanism of galanin's action. For example, galanin receptor ligands with selective antagonistic effects can be used to determine structural features of the galanin receptor that plays a role in the complex biological effects attributed to the receptor. Galanin receptor ligands also can be used in structure function analysis to identify key moieties or substituents that impart useful features for drug delivery in vivo, an analysis that can be conducted in an animal model.

There are various clinical uses for galanin receptor ligands of the invention. Galanin receptor ligands which have agonist activity can be used for treating various disorders or conditions. In the case of CNS, agonist ligands can be used to treat convulsive seizures such as arise in the case of epilepsy. Such invention compounds also may be used for CNS injuries or in open hear surgery to prevent anoxic damage. Galanin receptor ligand agonists also are useful in neuroendocrinology disorders. For example, dwarfism can be treated by administering a galanin agonist ligand which acts to increases release of growth hormone. Galanin receptor ligand agonists also can be used to treat endocrinology disorders that arise as a result of cancers that express galanin receptors. For example, the invention galanin receptor agonists can be used to control prolactin or insulin release from pituitary adenomas. Galanin receptor ligand agonists may be used as an analgesic for pain control. Invention compounds can be used, for example, to control the pain threshold or prolong the effect of other analgesics such as morphine. This may allow lower doses of morphine, which is particularly useful for treating chronic pain.

Galanin receptor ligands of the invention which have antagonist activity can be used for treating various disorders or conditions. Invention ligand antagonists can be used to improve cognitive function in Alzheimer's disease by improving cholinergic function negatively impacted by galanin. Invention ligand antagonists also may be used as antidepressants by, for example, enhancing firing of noradrenergic neurons or by suppressing 5-HT metabolism. Galanin receptor ligand antagonists can be used to treat feeding disorders or obesity by suppressing fat or carbohydrate intake.

In accordance with these uses, galanin receptor ligands can be formulated for pharmaceutical use by combining the receptor ligand with a pharmaceutically acceptable excipient (s). The excipients are selected by the manufacturer depending on the desired form of the preparation, e.g. tablets and solutions or suspensions for injection, and the desired route of administration, and examples of suitable excipients can be found in the US or European pharmacopoeia. In a presently preferred embodiment of the pharmaceutical preparation according to the invention, the preparation is in the form of an intraperitoneal injection solution.

Another aspect of the invention is to use the galanin receptor ligands as a medicament. Further, the medicament may be selected from the group consisting of medicaments for the treatment of diseases and disorders as described above including growth hormone release, insulin release, tumors expressing galanin receptors, pain states such as allodynia, psychiatric states such depression (e.g., where noradrenaline or serotonin activity need be modulated), and the like.

The galanin receptor ligands of the invention can be used prophylactically or therapeutically to treat the diseases or disorders discussed above by administering a prophylactically or therapeutically effective dose of a galanin receptor agonist according to the invention or a pharmaceutical preparation according to the invention, to the patient. The mammalian patient may be a human patient. The prophylactically or therapeutically effective anticonvulsant dose of a galanin receptor agonist or a pharmaceutical preparation of the invention will be recommended by the attending physician with guidance from the manufacturer and the response from the patient. Thus, the invention compounds may be administered in an effective does to a patient prophylactically or therapeutically to treat a disease or disorder related to seizures, growth hormone release, insulin release deviations, tumors expressing galanin receptors, pain states, allodynia, and noradrenaline or serotonin activity, and the like in a mammalian patient The invention will now be illustrated with experiments and accompanying drawings, but it should be understood that the invention is not limited to any specifically mentioned details.

EXAMPLES

Abbreviations commonly used in the field of chemistry and biology are used in this specification. In particular, the following abbreviations are used: AMC, 7-amino-4-methylcoumarin; Boc, tert-butoxycarbonyl; Cha, cyclohexylalanine; DCC, dicyclohexylcarbodiimide; DCM, dichloromethane; DIEA, diisopropylethylamine; DMF, N,N-dimethylformamide; DMSO, dimethylsulfoxide; Fmoc, 9-fluorenyimethoxycarbonyl; HOBt, 1-hydroxybenzotriazole; i.p., intraperitoneally; PTZ, pentylenetetrazole; TBTU, 2-(1H-Benzotriazole-1-yl)-1,1,3,3-tetramethyluronium tetrafluoroborate; TFA, trifluoroacetic acid.

A. Synthesis of galanin receptor agonists of the invention

The synthesis strategy is shown in FIG. 1 for the synthesis of galnon, and the synthesis of the compounds L138 and L131 followed essentially the same strategy.

The first step of the galnon synthesis was the coupling of Fmoc-Lys(Boc)-OH to AMC. 1 mmol of Fmoc-Lys(Boc)-OH and 0.5 equivalents of DCC were separately dissolved in dioxane, cooled on ice and then pooled. Reaction mixture was stirred for 30 min at room temperature, then 0.5 equivalents of AMC dissolved in DMF was added to the symmetric anhydride solution and the mixture was stirred overnight. Next day the solvents were evaporated, Fmoc-Lys(Boc)-AMC was precipitated with petrol ether/ethyl acetate mixture (5/95 v/v) and dried under vacuum. The Boc-group was removed with $H_2O$/TFA mixture (3/97 v/v) in ice bath for 5 mm, followed by the evaporation of the solvents. The obtained Fmoc-Lys-AMC was coupled to chlorotrityl resin by incubation of 2–3 equivalents of Fmoc-Lys-AMC, 4–9 equivalents of DIEA and 1 equivalent of chlorotrityl resin for 2 h. Resin was washed and the Fmoc-group was removed with piperidine/DMF (20/80 v/v). Coupling of Fmoc-Cha was performed using 2 equivalents of amino acid, TBTU, HOBt and 4 equivalents of DIEA.

Galnon was cleaved from the resin by applying TFA/DCM mixture (50/50 v/v) in four aliquots. The filtrate was evaporated and the obtained product was purified on Sep-Pak® Cartridges and analyzed using plasma desorption mass spectrometer (model Bioion 20, Bioion, Uppsala, Sweden).

B. Characterization of the biological properties of the agonists of the invention First, human and rat galanin were synthesized on the model 431A peptide synthesizer (Perkin Elmer Applied Biosystems Inc., Foster City, Calif.).

1. Ligand binding to galanin receptors, adenylate cyclase assay

The mixtures of ligands and individual compounds were screened to displace [$^{125}$I]-galanin in equilibrium binding assay using membrane preparations from rat hippocampi, rich in galanin binding sites as described in detail previously[11]. Effect of galnon on basal and forskolin-stimulated cAMP production were performed essentially as described by Valkna et al.[12] in membranes from rat ventral hippocampi.

2. Autoradiography

Rats were decapitated, the spinal cord lumbar segments L4 and L5 were dissected out, rapidly frozen, cut in a cryostat and processed for the autoradiographic ligand binding assay of Young and Kuhar[13], as described previously[14]. Galnon was added at 1, 3 and 5 µM concentration. The sections were processed in a BAS3000 Bio-Imagine Analyzer (Fuji) and quantified and then exposed to Hyperfilm-Max X-ray film (Arnersham Pharmacia Biotech).

3. Seizure induction and quantification

The experiments were performed on C57B1 male mice (weight 20–30 g). Animals to be treated with galanin, or M35 were anaesthetized with ketamine (100 mg/kg i.p.) and xylazine (15 mg/kg i.p.) and stereotaxically implanted i.c.v. with guide cannulae (0.6 mm internal diameter). Postoperative recovery was 3–5 days. Galanin, or M35 were injected into the lateral brain ventricle of freely moving mice by means of Hamilton microsyringe in the amount 0.5 nmol, in 0.5 µl, at a rate 0.5 min/min. Control animals were treated with saline.

Galnon was dissolved in the 50% DMSO in saline and administered i.p. in a dose of 2 mg/kg 15 mm prior to PTZ injection (when the effect of galnon alone was studied) or 5 mm after M35 injection (in co-administration studies). Control animals were treated with 50% DM50 in saline.

Seizures were induced by i.p. injection of PTZ (Research Biochemicals, Natick, Massachusetts) in a dose of 40 mg/kg (when studying the effects of galanin only, or galnon only) or 30 mg/kg (when studying the effect of M35 and galnon+M35). The animals were placed in individual Plexiglas cages and videotaped for 15 min after PTZ administration. Seizures were analyzed off-line by a unbiased investigator and quantified using the following scale: 0: no motor seizures; 1: staring, mouth, or facial movements; 2: head nodding or isolated twitches; 3: unilateral bilateral forelimb clonus; 4: rearing; 5: rearing and falling; 6: tonic extension of hind limbs or death. The latency of each behavioral seizure type and the highest seizure score were recorded. For statistical purposes, if the animal failed to show seizure of any particular score, the latency of 900 s (which was a period of observation) was assigned to this score. No obvious behavioral side effects of galnon were observed. Statistical methods used: t-test (latency) and Mann-Whitney (seizure score).

C. Summary of results

The synthesized compound galnon was tested for the ability to displace [$^{125}$I]-galanin from galanin receptors in rat ventral hippocampal membranes. [$^{125}$I]-Galanin was displaced by galnon in membranes from rat ventral hippocampus with a $K_i$ value 4.8 µM (Table 1).

The ability of galnon to displace [$^{125}$I]-galanin from its binding sites in a concentration-dependent manner was confirmed in an autoradiographic binding assay on rat spinal cord sections, where the autoradiographic signal of [$^{125}$I]-galanin and its dose-dependent displacement by galnon could be studied best. A significant increase in binding as compared to controls was only seen at the concentration of 5 µM.

Like galanin, galnon inhibited both basal and forskolin-stimulated adenylate cyclase activity (Table 1). Inhibition of adenylate cyclase activity suggested that galnon exhibited agonist-like properties at galanin receptor(s).

Figure 2:
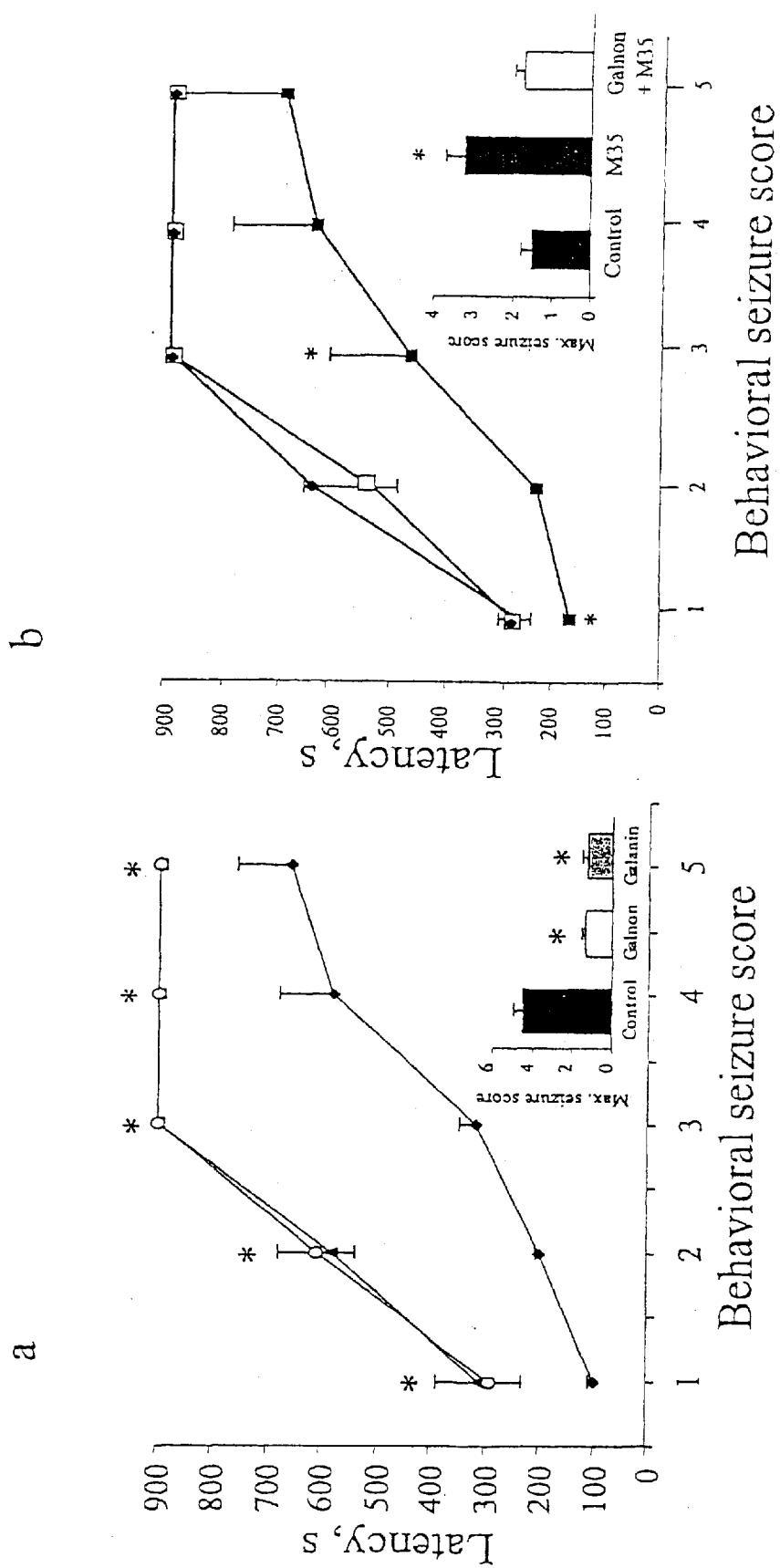
FIG. 2. Effects of galnon and/or M35 on PTZ-induced seizures on mice. Data are presented as mean±SEM. Inserts show maximal seizure scores (mean±SEM).

To study the potential agonist properties of galnon, we tested its anticonvulsant properties. To test anticonvulsant capability of galnon, we used pentylenetetrazol (PTZ)-induced convulsions in mice. In the first set of experiments, we induced seizures with 40 mg/kg of PTZ (i.p.), and injected 2 mg/kg of galnon (i.p.) 15 min prior to PTZ injection. The galnon treatment lowered the maximal seizure score from 4.5 (control mice) to 1.45 (galnon-treated mice), p<0.01 (FIG. 2a). The anticonvulsant effect of galnon was comparable to that of galanin administered i.c.v. in a dose 0.5 nmol.

The next set of experiments was designed to confirm that the antiepileptic activity of galnon is exerted at galanin receptors. Specifically, we co-administered M35 (i.c.v.), a galanin receptor antagonist that does not cross the blood-brain barrier, and galnon (i.p.). Seizures were then induced with 30 mg/kg PTZ. Galnon completely abolished the seizure-facilitating effect of M35 (FIG. 2b), the galanin antagonist that, as demonstrated earlier[6], potentiates PTZ induced seizures.

The effects of intrahippocampal galnon administration was evaluated in rats. SSSE consisted of recurrent limbic seizures of varying intensity (stages 1–5), which lasted for 12–18 h after PPS was discontinued. Behavioral seizures were accompanied by high-frequency (13+Hz) and amplitude (1+mV) discharges with the duration of individual events between 30 s and 3 min. Between the seizures, ictal spikes with the amplitude of 0.8 mV and more and frequency of 3 Hz and less were continuously generated (spike frequency of 3 Hz and more was recognized as a seizure)[5].

Figure 3A:
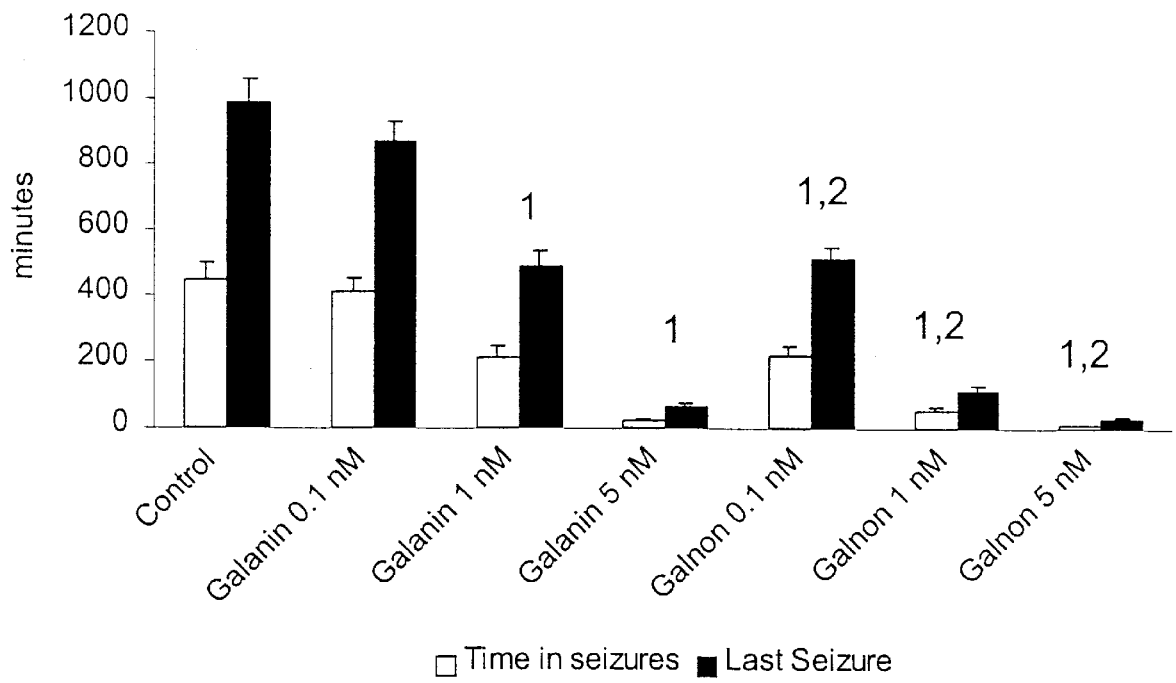
Figure 3B:
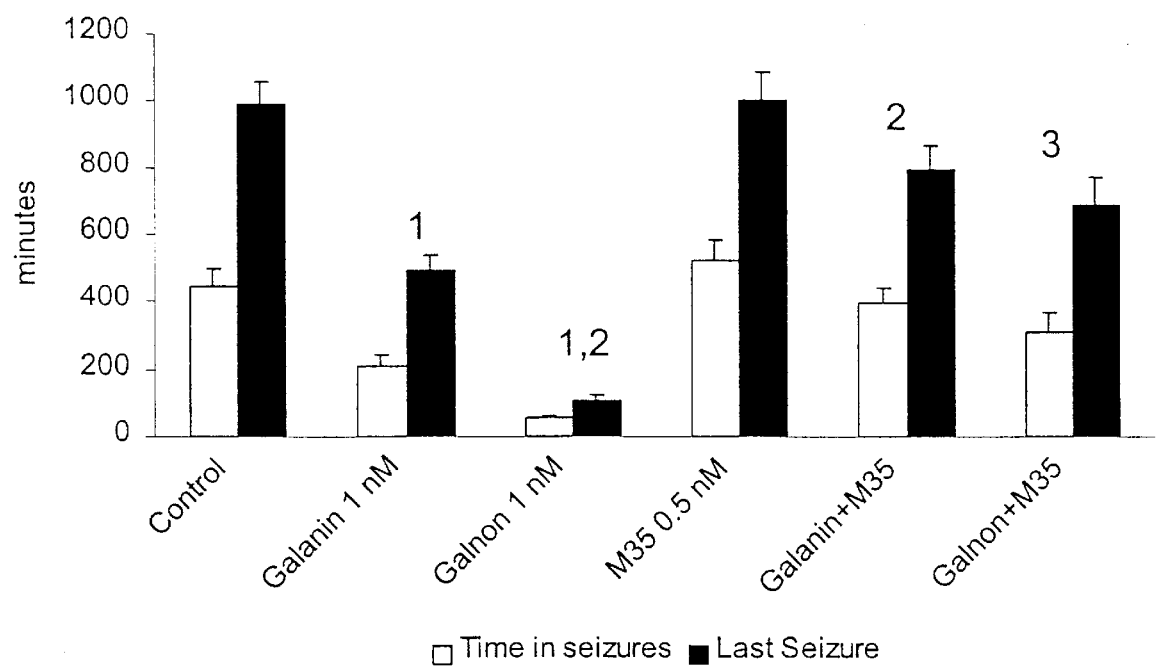

Intrahippocampal administration of galnon shortened the duration of SSSE and decreased the time spent in seizures in a dose-dependent manner (FIG. 3a). In the maximal dose used (5 nmol), galnon shortened SSSE duration to 28±8 min, from 760±77 min in controls (P<0.05). The anticonvulsant effects of galnon were abolished by pretreatment with the galanin receptor antagonist M35, when the latter was administered in a dose that alone, as it had been previously reported[5], did not alter the course of SSSE (0.5 nmol, FIG. 3b). When galnon was injected immediately after M35, both time spent in seizures and the duration of SSSE were significantly higher than in galnon-treated rats without M35, and these parameters did not differ from those in control animals (FIG. 3b).

Figure 3C:
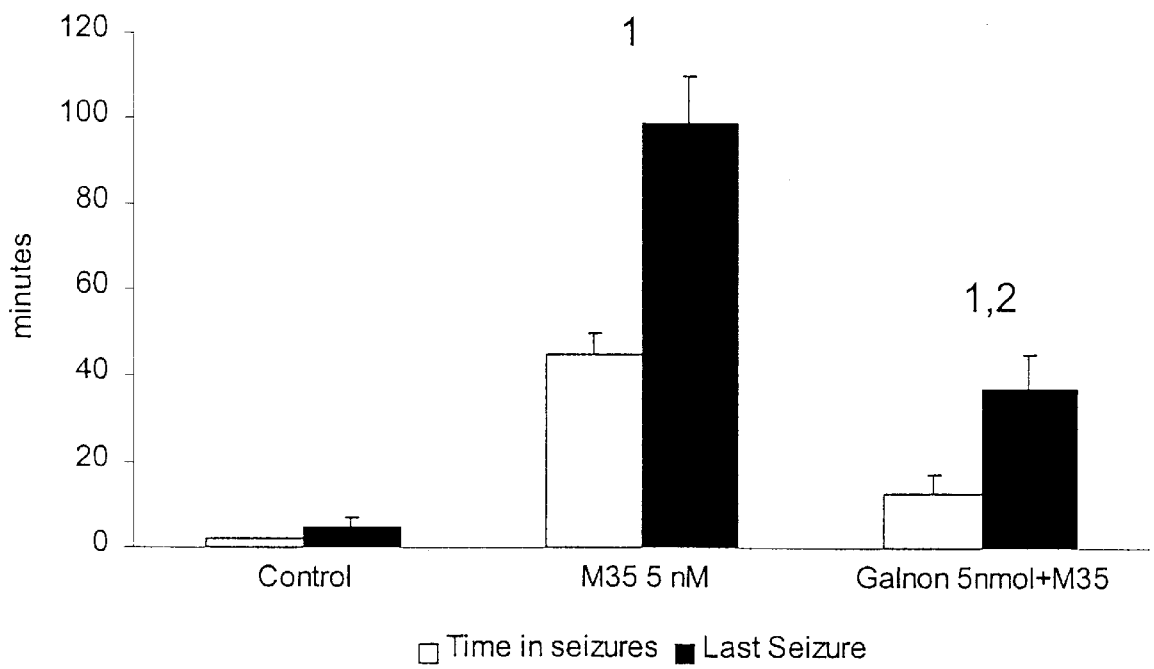

In a separate set of experiments, equimolar galnon blocked the seizure-facilitating effect of intrahippocampal injections of M35 in an amount of 5 nmol, a dose, which was previously shown to potentiate seizures[6]: under these conditions PPS as short as 7 min is sufficient to induce self-sustaining seizures[6]. When an equimolar amount of galnon was administered into the hippocampus before M35, total seizure time and duration of SSSE were reduced from 45±5 to 13±4 min and from 99±11 to 37±8 min, respectively (FIG. 3c).

We examined the anticonvulsant effects of galnon in SSSE. As shown previously, down-regulation of GalR1 by PNA1 did not affect the parameters of SSSE[5]. However, in PNA1-pretreated animals, galnon (1 nmol) had no effect on self-sustaining seizures, whereas in control rats injected with scrambled PNA, galnon reduced total seizure time 9-fold and duration of SSSE 7-fold.

In summary, the synthesis of galnon, Fmoc-Cha-Lys-amidomethylcoumarin, a low molecular weight, blood brain barrier-penetrating galanin receptor ligand with agonist properties, both in vitro and in vivo is described. Galanin exerts inhibitory effects on excitatory transmission by inhibition of glutamate release in the ventral hippocampus, by hyperpolarization of granule as well as of pyramidal cells through enhanced K+ conductance and reduced L-type $Ca^{2+}$ channel opening. Therefore, galanin receptor agonists are expected to act as very potent antiepileptic agents in seizures of different origins. The experiments herein show that a systemically active galanin receptor agonist is a potent anticonvulsant against PTZ-induced seizures in mice, and is useful in a broad spectrum of seizure and epilepsy models.

The invention thus has been disclosed broadly and illustrated in reference to representative embodiments described above. Those skilled in the art will recognize that various modifications can be made to the present invention without departing from the spirit and scope thereof. All publications, patent applications and issued patents, are herein incorporated by reference to the same extent as if each individual publication, patent application or issued patent were specifically and individually indicated to be incorporated by reference in its entirety. Swedish patent application serial no. 01011856-3 filed on May 25, 2001 entitled "Galanin Receptor Agonist," and U.S. provisional patent application serial no. 60/372237 filed on Apr. 12, 2002 entitled "Non-Natural Galanin Receptor Ligands," are herein incorporated by reference in their entirety.

D. References

1. Tatemoto, K., Rökaeus, A, Jörnvall, H., McDonald, T. J. & Mutt, V. Galanin—a novel biologically active peptide from porcine intestine. *FEBS Lett.* 164, 124–128 (1983).

2. Bartfai, T. & Langel, Ü. Galanin receptor ligands as potential therapeutic agents in depression and neurodegeneration. *Eur. J Med. Chem.* 30, S163–S174 (1995).

3. Bartfai, T. Galanin: a neuropeptide with important central nervous system actions, in *Psychopharmacology: the Fourth Generation of Progress* (eds Bloom, F. E. & Kupfer, D. J.) 563–571 (Raven Press, 1185 Ave of the Americas, New York, N.Y. 10036, 1995).

4. Langel, Ü. & Bartfai, T. Chemistry and molecular biology of galanin receptor ligands. *Ann. NY Acad. Sci.* 863, 86–93 (1998).

5. Mazarati, A. et al Galanin modulation of seizures and seizure modulation of hippocampal galanin in an animal model of status epilepticus. *J. Neurosci.* 18, 10070–10077 (1998).

6. Mazarati, A. M. et al Modulation of hippocampal excitability and seizures by galanin. *J. Neurosci.* 20, 6276–81 (2000).

7. Zini, S., Roisin, M. P., Langel, Ü., Bartfai, T. & Ben-An, Y. Galanin reduces release of endogenous excitatory amino acids in the rat hippocampus. *Eur. J. Pharmacol-Molec. Pharm.* 245, 1–7 (1993).

8. Xu, Z. Q., Ma, X., Soomets, U., Langel, Ü. & Hökfelt, T. Electrophysiological evidence for a hyperpolarizing, galanin (1–15)-selective receptor on hippocampal CA3 pyramidal neurons. *Proc. NatL Acad. Sci. USA* 96, 14583–7 (1999).

9. Chu, M. et al A new fungal metabolite, Sch 202596, with inhibitory activity in the galanin receptor GalR1 assay. *Tetrahedron Lett.* 38, 6111–6114 (1997).

10. Scott, M. K. et al 2,3-Dihydro-dithiin and -dithiepine-1,1,4,4-tetroxides: small molecule non-peptide antagonists of the human galanin hGAL-1 receptor. *Bioorg. Med. Chem.* 8,1383–91 (2000).

11. Land, T., Langel, Ü, Fisone, G., Bedecs, K. & Bartfai, T. Assay for galanin receptor. *Methods in Neurosciences* 5, 225–234 (1991).

12. Valkna, A. et al. Differential regulation of adenylate cyclase activity in rat ventral and dorsal hippocampus by rat galanin. *Neurosct Lett.* 187, 75–78 (1995).

13. Young, W. S., 3rd & Kuhar, Mi'. A new method for receptor autoradiography: [3H]opioid receptors in rat brain. *Brain Res.* 179, 255–270. (1979).

14. Pooga, M. et al Cell penetrating PNA constructs regulate galanin receptor levels and modify pain transmission in vivo. *Nature Biotechnology* 16, 857–861 (1998).

15. Land, T. et al Linear and cyclic N-terminal galanin fragments and analogs as ligands at the hypothalamic galanin receptor. *Int. J Peptide Protein Res.* 38, 267–272 (1991).

16. Valkna, A. et al Effects of chimenic galanin receptor ligands on basal adenylate cyclase activity in rat ventral hippocampal membranes. *Protein Peptide Lett.* 2, 267–274 (1995).

TABLE 1

Comparison of galanin and galnon in binding to galanin receptors and inhibiting adenylate cyclase (basal and forskolin stimulated) in membranes from rat ventral hippocampi.

| | Galanin, rat [15,16] | Galnon |
| --- | --- | --- |
| MW, Da | 3209 | 677 |
| $K_i$, M | $0.8 \cdot 10^{-9}$ | $4.8 \pm 0.6 \cdot 10^{-6}$ |
| $EC_{50}$, M of inhibition of adenylate cyclase activity | $1.1 \cdot 10^{-9}$ (basal) $1.1 \cdot 10^{-9}$ (forskolin stimulated) | $8.0 \pm 3.0 \cdot 10^{-6}$ (basal) $10 \pm 3 \cdot 10^{-6}$ (forskolin stimulated) |

We claim:

1. A compound which is a galanin receptor ligand having the formula:

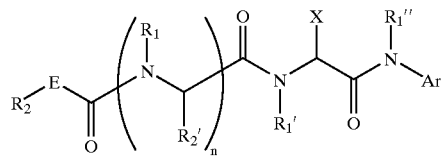

wherein:

$R_1$, $R_1'$, and $R_1''$ are each independently hydrogen or lower alkyl, $R_2$ is an optionally substituted hydrocarbyl moiety containing at least about four carbon atoms, $R_2'$ is an optionally substituted hydrocarbyl moiety containing at least four carbon atoms, E is optional, and, if present, is O or S, X is a lysine side chain, Ar is an optionally substituted aromatic or heteroaromatic moiety having at least about three carbon atoms, and n is 1 to 3.

2. A compound according to claim 1, wherein $R_2$ is an optionally substituted branched chain hydrocarbyl moiety.

3. A compound according to claim 1, wherein $R_2$ is an optionally substituted cyclic hydrocarbyl moiety.

4. A compound according to claim 3, wherein said cyclic moiety is cycloalkyl, heterocyclic, aromatic, or heteroaromatic.

5. A compound according to claim 4, wherein said cyclic moiety is polycyclic.

6. A compound according to claim 4, wherein said cyclic moiety is aromatic.

7. A compound according to claim 1, wherein $R_2'$ contains at least six carbon atoms.

8. A compound according to claim 7, wherein $R_2'$ is an optionally substituted straight or branched chain hydrocarbyl moiety.

9. A compound according to claim 7, wherein $R_2'$ is an optionally substituted cyclic moiety.

10. A compound according to claim 9, wherein said cyclic moiety is cycloalkyl, heterocyclic, aromatic, or heteroaromatic.

11. A compound according to claim 1, wherein said Ar is optionally substituted aromatic.

12. A compound according to claim 11, wherein said Ar is optionally substituted phenyl or naphthyl.

13. A compound according to claim 1, wherein said Ar is optionally substituted heteroaromatic.

14. A compound according to claim 13, wherein said Ar is chromenyl, furyl, thiophenyl, oxadiazolyl, benzoxazyl, benzofuryl, benzodioxolyl, imidazolyl, benzimidazolyl, pyrrolyl, thienyl, thiazolyl, oxazolyl, isoxazolyl, triazolyl, benzotriazolyl, indolyl, pyrimidinyl, pyrazolyl, quinolinyl, isoquinolinyl, quinazolinyl, or pyridyl.

15. A compound according to claim 1, where $R_2$ and $R_2'$ are substituted with a hydrocarbyl moiety containing at least about four carbon atoms comprising a selected from the group consisting of hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, oxo, cyano, nitro, amino, amido, C(O)H, acyl, oxyacyl, carboxyl, carbamate, sulfonyl, sulfonamide, or sulfuryl.

16. A compound according to claim 1, wherein n is 1.

17. A compound according to claim 1 having a molecular weight of 700 daltons or less.

18. A compound according to claim 1 which crosses the blood-brain barrier.

19. A compound according to claim 1 having the formula

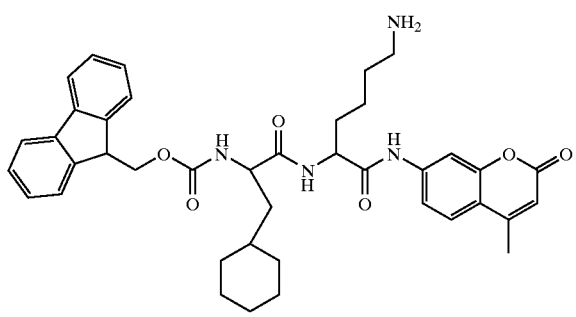

(1-[5-amino-1-(4-methyl-2-oxo-2H-chromen-7-ylcarbamoyl)-pentylcarbamoyl]-2-cyclohexyl-ethyl-carbamic acid 9H-fluoren-9-ylmethyl ester).

20. A compound according to claim 1 having the formula

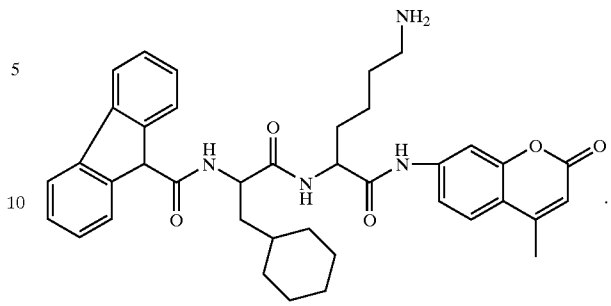

21. A compound according to claim 1 having the formula

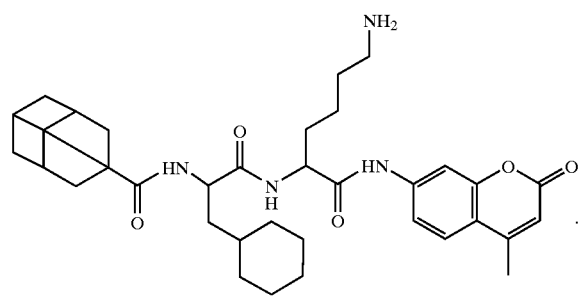

22. A compound according to claim 1 having the formula

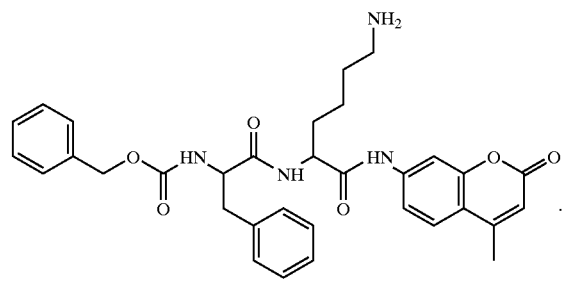

23. A pharmaceutical preparation comprising the compound according to claim 1 and a pharmaceutically acceptable excipient(s).

24. A pharmaceutical preparation according to claim 23 in the form of an intraperitoneal injection solution.

25. The compound according to claim 1 for use as a medicament.

26. The compound according to claim 25, wherein the medicament is selected from the group consisting of anticonvulsant and antiepileptic agents.

27. The compound according to claim 25, wherein the medicament is selected from the group consisting of medicaments for the treatment of diseases and disorders related to growth hormone release, insulin release, tumors expressing galanin receptors, pain states, allodynia psychiatric states, cognition, and feeding.

28. A method of prophylactically or therapeutically treating a disease or disorder resulting in convulsive seizures in a mammalian patient, comprising administering a prophylactically or therapeutically effective anticonvulsant dose of the compound according to claim 1 or a pharmaceutical preparation according to claim 19 to the patent.

29. The method according to claim 28, wherein the convulsive seizures are due to epilepsy.

30. A method of prophylactically or therapeutically treating a disease or disorder related to growth hormone release, insulin release, tumors expressing galanin receptors, pain states, allodynia, psychiatric states, cognition, and feeding in a mammalian patient, comprising administering a prophylactically or therapeutically effective dose of the compound according to claim 1 or a pharmaceutical preparation according to claim 23 of the patent.

31. A compound which is a galanin receptor ligand having the formula:

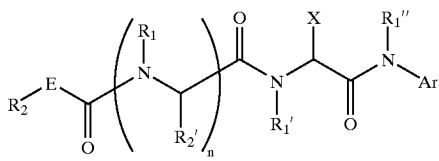

wherein:
- $R_1$, $R_1'$, and $R_1''$ are each independently hydrogen or lower alkyl,
- One of $R_2$ and $R_2'$ is an optionally substituted polycyclic hydrocarbyl moiety containing at least about four carbon atoms, and the other of $R_2$ and $R_2'$ is an optionally substituted hydrocarbyl moiety containing at least about four carbon atoms,
- E is optional, and, if present, is O or S,
- X is a hydrocarbyl moiety bearing at least one substituent, wherein at least one of said substituents bears a positive charge,
- Ar is an optionally substituted aromatic or heteroaromatic moiety having at least about three carbon atoms, and n is 1 to 3.

32. A compound according to claim 31, wherein said polycyclic moiety is cycloalkyl, heterocyclic, aromatic, or heteroaromatic.

33. A compound according to claim 32, wherein said polycyclic moiety is aromatic.

34. A compound according to claim 31, wherein $R_2'$ contains at least six carbon atoms.

35. A compound according to claim 34, wherein $R_2'$ is an optionally substituted straight or branched chain hydrocarbyl moiety.

36. A compound according to claim 34, wherein $R_2'$ is an optionally substituted cyclic moiety.

37. A compound according to claim 36, wherein said cyclic moiety is cycloalkyl, heterocyclic, aromatic, or heteroaromatic.

38. A compound according to claim 31, wherein X is a straight or branched chain alkyl.

39. A compound according to claim 38, wherein said substituent is amine, hydroxy, or thiol.

40. A compound according to claim 38, wherein said substituent is amine.

41. A compound according to claim 31, wherein said Ar is optionally substituted aromatic.

42. A compound according to claim 41, wherein said Ar is optionally substituted phenyl or naphthyl.

43. A compound according to claim 31, wherein said Ar is optionally substituted heteroaromatic.

44. A compound according to claim 43, wherein said Ar is chromenyl, furyl, thiophenyl, oxadiazolyl, benzoxazyl, benzofuryl, benzodloxolyl, imidazolyl, benzimidazolyl, pyrrolyl, thienyl, thiazolyl, oxazolyl, isoxazoly, triazolyl, benzotriazolyl, indolyl, pyrimidinyl, pyrazolyl, quinolinyl, isoquinolinyl, quinazolinyl, or pyridyl.

45. A compound according to claim 31, where $R_2$ and $R_2'$ are substituted with a hydrocarbyl moiety containing at least about four carbon atoms comprising a selected from the group consisting of hydroxy, alkoxy, mercapto, cycloalkyl, substituted cycloalkyl, heterocyollo, substituted heterocyclic, aryl, substituted aryl, heteroaryl, substituted heteroaryl, aryloxy, substituted aryloxy, halogen, oxo, cyano, nitro, amino, amido, C(O)H, acyl, oxyacyl, carboxyl, carbamate, sulfonyl, sulfonamide, or sulfuryl.

46. A compound according to claim 31, wherein n is 1.

47. A compound according to claim 31 having a molecular weight of 700 daltons or less.

48. A compound according to claim 31 which according to which crosses the blood-brain barrier.

49. A compound according to claim 31 having the formula

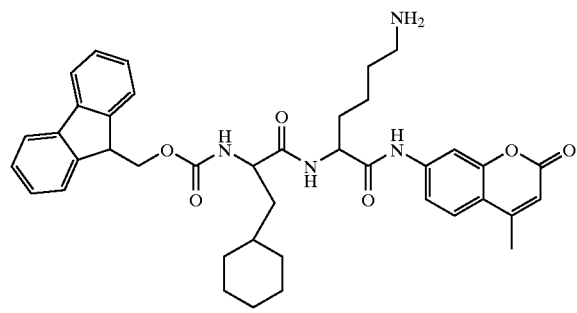

(1-[5-amino-1-(4-methyl-2-oxo-2H-chromen-7-ylcerbamoyl)-pentylcarbamoyl]-2-cyclohexyl-ethyl-carbamic acid 9H-fluoren-9-ylmethyl ester).

50. A compound according to claim 31 having the formula

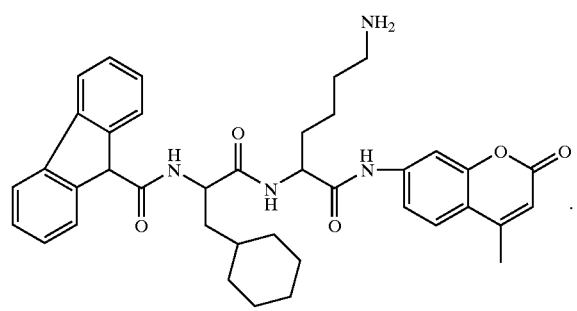

51. A compound according to claim 31 having the formula

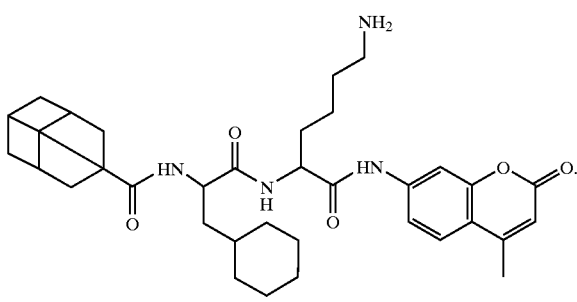

52. A pharmaceutical preparation comprising the compound according to claim 31 and a pharmaceutically acceptable excipient(s).

53. A pharmaceutical preparation according to claim 52 in the form of an intraperitoneal injection solution.

54. The compound according to claim 31 for use as a medicament.

55. The compound according to claim 54, wherein the medicament is selected from the group consisting of anticonvulsant and antiepileptic agents.

56. The compound according to claim 54, the medicament is selected from the group consisting of medicaments for the treatment of diseases and disorders related to growth hormone release, insulin release, tumors expressing galanin receptors, pain states, allodynia psychiatric states, cognition, and feeding.

57. A method of prophylactically or therapeutically treating a disease or disorder resulting in convulsive seizures in a mammalian patient, comprising administering a prophylactically or therapeutically effective anticonvulsant dose the compound according to claim 34 or a pharmaceutical preparation according to claim 49 to the patent.

58. The method according to claim 57, wherein the convulsive seizures are due to epilepsy.

59. A method of prophylactically or therapeutically treating a disease or disorder related to growth hormone release, insulin release, tumors expressing galanin receptors, pain states, allodynia, psychiatric states, cognition, and feeding in a mammalian patient, comprising administering a prophylactically or therapeutically effective dose of the compound according to claim 31 or a pharmaceutical preparation according to claim 55 of the patent.

* * * * *

UNITED STATES PATENT AND TRADEMARK OFFICE
CERTIFICATE OF CORRECTION

PATENT NO. : 6,747,060 B2
DATED : June 8, 2004
INVENTOR(S) : Kulliki Saar et al.

It is certified that error appears in the above-identified patent and that said Letters Patent is hereby corrected as shown below:

Column 15,
Line 64, replace "benzodloxolyl" with -- benzodioxolyl --.
Line 65, replace "isoxazoly" with -- isoxazolyl --.

Column 16,
Line 5, replace "heterocyollo" with -- hererocyclic --.
Line 13, replace "which according to which" with -- which --.
Line 30, replace "ylcerbamoyl" with -- ylcarbamoyl --.

Column 17,
Line 4, replace "claim 54, thye medicament" with -- claim 54 wherein the medicament --.
Line 13, replace "dose the" with -- dose of the --.

Signed and Sealed this

Twenty-fourth Day of August, 2004

JON W. DUDAS
*Director of the United States Patent and Trademark Office*